United States Patent [19]

Hoch et al.

[11] 4,418,703
[45] Dec. 6, 1983

[54] MULTIPLE SAMPLE NEEDLE ASSEMBLY

[75] Inventors: Louis Hoch, Nutley; Lawrence Lutkowski, East Rutherford, both of N.J.

[73] Assignee: Becton Dickinson and Company, Paramus, N.J.

[21] Appl. No.: 288,635

[22] Filed: Jul. 30, 1981

[51] Int. Cl.³ .................................................. A61B 5/14
[52] U.S. Cl. ...................................... 128/766; 128/763
[58] Field of Search ................................. 128/760–763, 128/768

[56] References Cited

U.S. PATENT DOCUMENTS

| | | | |
|---|---|---|---|
| 3,494,352 | 2/1970 | Russo et al. | 128/764 |
| 3,659,587 | 5/1972 | Baldwin | 128/764 |
| 4,166,450 | 9/1979 | Abramson | 128/764 |
| 4,190,048 | 2/1980 | Sampson | 128/218 NV |
| 4,207,870 | 6/1980 | Eldridge | 128/766 |

FOREIGN PATENT DOCUMENTS 2455631  5/1976  Fed. Rep. of Germany ...... 128/766

*Primary Examiner*—Kyle L. Howell
*Assistant Examiner*—John C. Hanley

[57] ABSTRACT

A multiple sample needle assembly includes a housing with a chamber therein. A first cannula for insertion into a liquid source is in fluid communication with the chamber. A second cannula is movably positioned in the housing and is out of liquid communication with the chamber when in a first position. A liquid flow mechanism inside the chamber is operatively responsive to inward movement of the second cannula to a second position for allowing liquid to flow from the chamber into the second cannula. After the liquid has been collected, the flow control mechanism automatically returns the second cannula to the first position.

8 Claims, 5 Drawing Figures

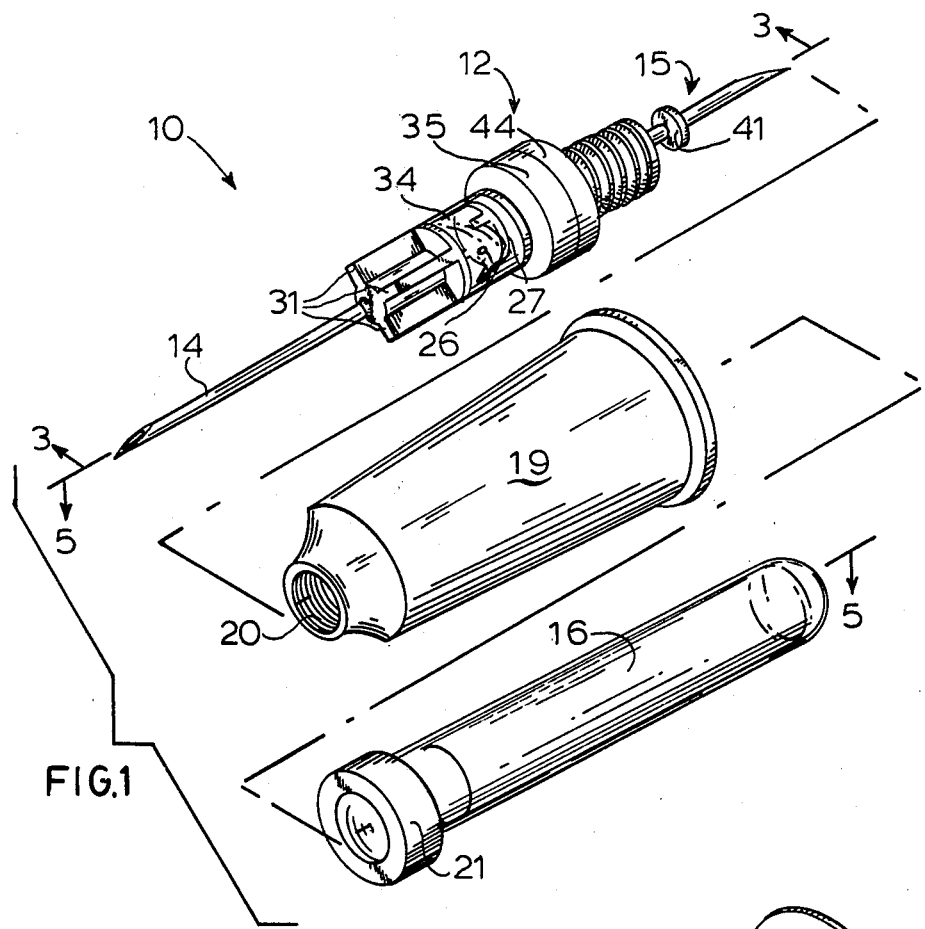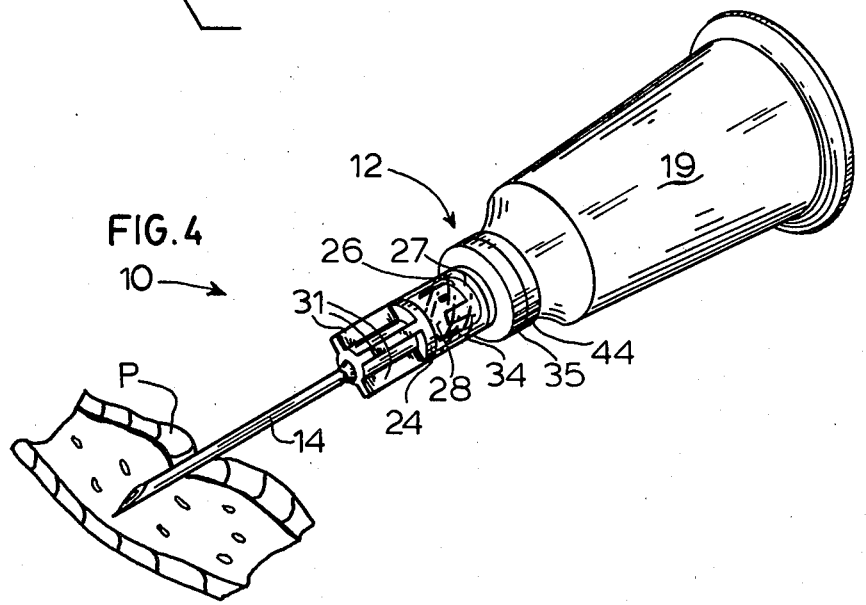

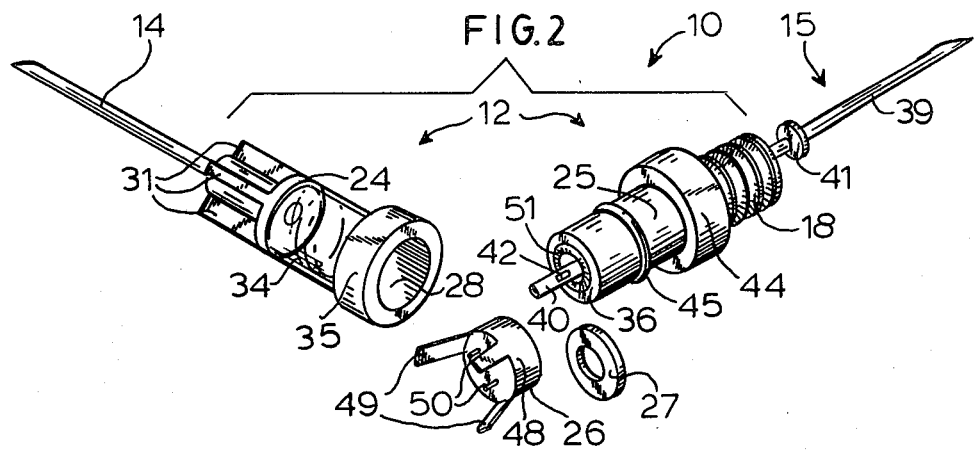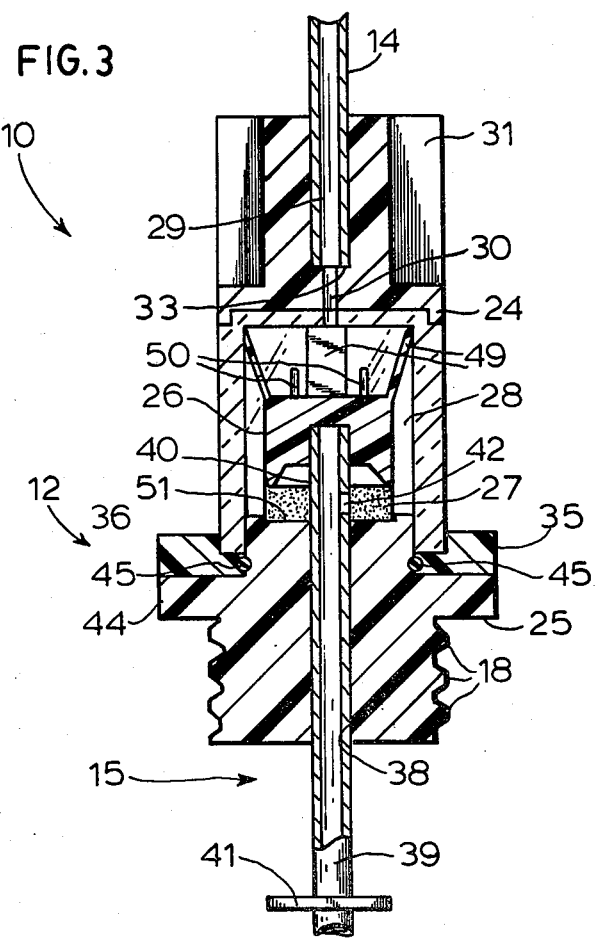

MULTIPLE SAMPLE NEEDLE ASSEMBLY

BACKGROUND OF THE INVENTION

1. Field of the Invention

The present invention relates to a needle assembly of collecting fluid such as from a patient, and more particularly, concerns a needle assembly for collecting multiple samples of blood from a patient into evacuated tubes without leaking blood while the tubes are being changed, and with a provision for indicating the entry of the needle assembly into the vein of the patient.

2. Description of the Prior Art

It is now standard practice to collect multiple samples of fluid, such as blood, from a patient in a single procedure. Once the needle is inserted into the vein of the patient, successive evacuated blood collection tubes are inserted into a holder which is connected to the needle and is adapted to receive these evacuated tubes therein. As each filled tube is removed from the holder, the needle remains inserted into the patient's vein. Various valves are now in use which prevent blood from flowing out of the holder during the time between removal of the filled tube and insertion of the next evacuated tube for collection of the subsequent sample. Elastomeric sleeves over an interior needle commonly serve this valve purpose. It is appreciated that, while the known valves for multiple sample needle assemblies perform satisfactorily, different ways are being sought to provide improvements in these devices.

U.S. Pat. Nos. 4,166,450; 4,099,520; 3,557,778; and 3,528,404 disclose representative blood sampling devices through which the flow of blood can be controlled during the collection of multiple samples.

In addition, it is also desirable to provide a mechanism whereby the user of a multiple sample needle assembly can be informed when the intravenous needle has penetrated the vein of the patient. Many times in collecting blood from a patient it is difficult to locate the vein or for other reasons blood flow into the collection device is minimal. In these instances, it becomes most advantageous to be able to make a quick determination that entry into the vein has been made and that blood is flowing into the needle assembly. Once this determination has been made and vein entry indeed accomplished, the evacuated blood collection container can then be inserted into the collection assembly in accordance with these well known techniques of collecting multiple blood samples during a single collection procedure.

One of the problems which arises during the venipuncture step concerns the pocket of air which is found in various needle assemblies useful for multiple sample blood collections. When venipuncture is made, and the evacuated blood collection container is not yet attached to the opposite end of the needle structure, blood cannot always flow into the needle assembly because of this pocket of air, which, under normal atmospheric conditions, remains inside the needle assembly. Accordingly, even though vein entry may have been accomplished, the blood may not move through the intravenous needle into the collection assembly under tourniquet pressure until the evacuated blood collection container is attached, whereupon the vacuum source causes sufficient draw through the needle assembly. It is thus desirable to provide a mechanism for purging the air from inside the needle assembly so that blood can readily flow into the assembly as it displaces the air.

SUMMARY OF THE INVENTION

The multiple sample needle assembly of the present invention is useful in collecting liquid samples from a source. This needle assembly comprises a housing with a chamber therein, and a first cannula for insertion into a liquid source in fluid communication with the chamber. A second cannula is movably positioned in the housing and is out of liquid communication with the first chamber when in a first position. Means inside the chamber, operatively responsive to inward movement of the second cannula to a second position, allows liquid to flow from the chamber into the second cannula. After the liquid has been collected, the second cannula is automatically returned to the first position.

In a preferred embodiment of the present invention, the housing has a forward end, a rearward end and a chamber within. The housing is translucent at least around the chamber so that the chamber is viewable by a user of the assembly. The first cannula extends outwardly from the forward end and is adapted for insertion into a patient. There is an exterior portion on the second, slidable cannula extending outwardly from the rearward end, while there is an interior portion extending inwardly into the chamber with an access opening. Associated with the rearward end of the housing is means for preventing liquid communication between the chamber and the access opening when the access opening is in a first position, however, this means provides a fluid communication between the chamber and the access opening when the access opening is in a second position inwardly displaced from the first position. Resilient means include the chamber normally biases the second cannula in an outward direction so that the access opening is in the first position. This resilient means is adapted to contract or deflect when the second cannula slides inwardly under an applied force so that the excess opening can be moved to the second position. Furthermore, the resilient means is adapted to urge the second cannula outwardly when the applied force is removed to move the access opening once again to the first position.

From the structural standpoint, the multiple sample needle assembly of the present invention is notably different from prior devices intended for the same purposes. In particular, the present invention relies essentially on mechanical movement of the various flow control elements in order to properly function. This, of course, is different from other devices which rely upon pressure differentials to cause various valves to operate. Moreover, the flow control mechanism is internal to the present assembly, whereas various prior art assemblies have relied upon an external, elastomeric resilient sleeve over the outside surface of the needle. In a preferred embodiment of the present invention, provides is made for a visual indicator of blood inside the assembly when the intravenous needle makes entry into a vein of the patient. Most advantageously, in the multiple sample blood collection procedure, the present invention prevents blood from leaking during the change of blood collection containers while the needle assembly remains inserted into the patient. The present invention provides for automatic flow control so that blood is prevented from leaking out of the chamber after a filled blood collection container is removed from the assembly. Other advantages are offered as well.

BRIEF DESCRIPTION OF THE DRAWINGS

FIG. 1 is an exploded perspective view illustrating the preferred multiple sample needle assembly, a holder for an evacuated container and an evacuated blood collection container for use in obtaining blood samples from a patient;

FIG. 2 is an exploded perspective view illustrating the components of the preferred multiple sample needle assembly of the present invention;

FIG. 3 is an enlarged cross-sectional view taken along line 3—3 of FIG. 1;

FIG. 4 is a perspective view of the needle assembly connected to a holder inserted into a patient so that a user can view same for indication of vein entry.

DETAILED DESCRIPTION

Figure 5:
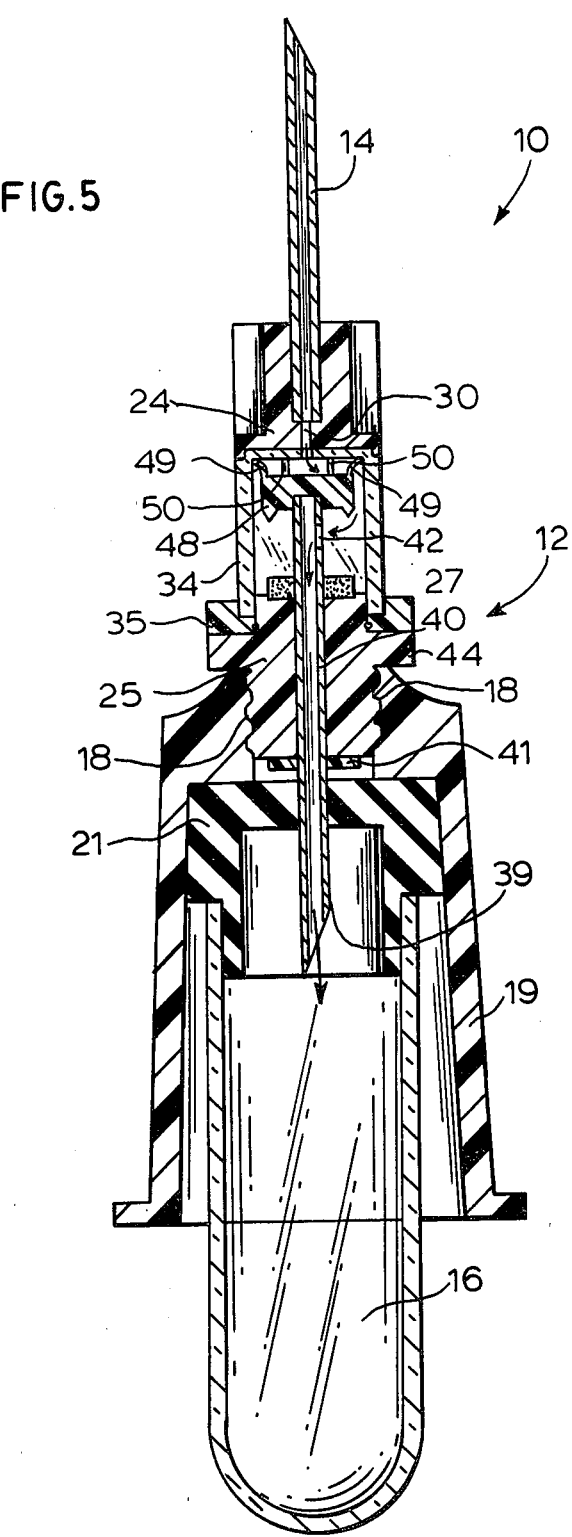
FIG. 5 is a cross-sectional view taken along line 5—5 of FIG. 1 with the components in an assembled condition as they would appear during use.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, particulary to FIG. 1, there is illustrated the preferred embodiment of a multiple sample needle assembly 10. The basic external components of needle assembly 10 include a housing 12, a first needle cannula 14 adapted for insertion into a patient and a second needle cannula 15 at the opposite end of housing 12, the second needle cannula adapted for penetratioin of an evacuated container 16 for collection of a blood sample. Housing 12 includes a threaded portion 18 adjacent second cannula 15 onto which a container holder 19 is threaded by its internal mating threads 20 at the forward end of the holder. Evacuated container 16 slides into holder 19 so that second needle cannula 15 can penetrate the penetrable stopper 21 at the forward end of the evacuated container. These general aspects of multiple sample blood collections in this type of structure are well known to those skilled in this art.

In FIGS. 2 and 3, the detailed construction of needle assembly 10 is illustrated. Housing 12 has a forward end 24 and a rearward end 25, these ends being preferably separable in order to place a resilient spring member 26 and porous plug 27 in their proper positions. Forward end 24 is preferably cylindrically shaped and has a large bore extending into and partially through its body. This bore serves as a chamber 28 within housing 12 after the components are assembled. At the other end of this section a smaller bore 29 is included which is generally sized to fit needle cannula 14 therein. In this embodiment being described, smaller bore 29 does not extend completely through forward end 24 to communicate with chamber 28. However, a still smaller diameter channel 30 interconnects these two bores so that there is fluid communication from hollow needle cannula 44 into chamber 28. At the junction between bore 29 and channel 30 a shoulder 33 is formed. Needle cannula 14 abuts against this shoulder 33 for proper positioning. Once needle cannula 14 is in position it can be suitably affixed, such as by adhesive means or the like. It is appreciated that the presence of channel 30 is not essential to the structure of this forward end of the housing, but is merely a preferable element. However, it will be appreciated that the diameter of channel 30 can be varied to provide a regulation of the fluid flow rate which flows therethrough.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into the tube holder. A portion 34 of the forward end surrounding chamber 28 is preferably smooth and translucent or transparent so that a user of this assembly can view the interior of the housing. In many situations, it may be preferable to make the entire forward end, and even possibly the rearward end, out of translucent or transparent material for ease of manufacture and to minimize the different types of materials which may be used in this assembly. Translucent rigid plastic is the most desirable material for inclusion in this assembly. Various sealed windows, ports or other means for a user to view the contents of the chamber are within the purview of this invention. It is preferable that such window or port be sealed so that any blood which enters chamber 28 upon the needle entering the vein will not escape from this assembly. Forward end 24 also includes an annular flange 35 which serves to provide a surface for joining the two portions of the housing together upon assembly. Once again, suitable fastening means, such as adhesives or the like may be used to secure the two portions of the housing together.

Rearward end 25 includes a short protruding portion 36, generally cylindrically shaped, and sized to fit within chamber 28 of the forward end upon assembly of the components together. At the opposite side of this rearward end, external threads 18 are provided as previously mentioned as a connection mechanism to the tube holder. A bore 38 extends through rearward end of the housing. This bore is sized to accept the diameter of second needle cannula 15 which freely slides in this rearward end through bore 38. Second needle cannula 15 is divided into two portions, an exterior portion 39 extending outwardly from the rearward end and an interior portion 40 extending inwardly into the chamber upon assembly of the components. On exterior portion 39 an annular ring 41 is provided which is spaced a short distance from the end of the threaded portion of the rearward end. This ring facilitates the inward movement of the second needle cannula during use of this assembly. An access opening 42 extends through the side of interior portion 40 into the lumen of the second needle cannula. This access opening provides liquid communication between chamber 28 and second cannula 15 when the second cannula slides inwardly into the chamber during use. An annular flange 44 is provided to cooperate with flange 35 in joining the two ends of the housing together. To assure proper fluid flow through the housing, an annular, elastomeric ring 45 may be included in this embodiment around protruding portion 36. Upon assembling the forward end and the rearward end together, with spring member 26 and porous plug 27 placed in their proper positions, respective flanges 35 and 44 are secured together by appropriate fastening means, such as adhesives or the like.

Spring member 26 preferably includes a hub portion 48 and a plurality of leaf springs 49 extending radially from hub 48. Hub 48 contacts interior portion 40 of the second needle cannula; instead of mere contact, hub 48 may be affixed to the interior portion of the second cannula and may even be permanently molded thereto. In this fashion, the lumen through the second cannula is sealed off at the end of the interior portion which extends into the chamber. Thus, the only mechanism for liquid communication between chamber 28 and second needle cannula 15 is through access opening 42, preferably located through the side wall of the interior portion of this second needle cannula. Resilient leaf springs 49 extend from hub 48 and contact the wall of the housing surrounding the chamber. In the normal, relaxed condition, leaf springs 49, illustrated as three in number in the present embodiment (although the number can be varied), are substantially expanded to bias the second needle cannula outwardly as illustrated in FIG. 3. Expanding upwardly from hub 48 are two stops 50 which serve to prevent the hub from completely seating against the opening at channel 30 during the use of this needle assembly.

As mentioned above, it is most desirable to provide a mechanism to remove air which may be inside the chamber during the initial stages when blood is drawn into the assembly. To this end, the preferred embodiment of the present invention includes a porous plug 27 which is seated in a recess 51 in protruding portion 36 of the rearward end of the housing. In the arrangement illustrated in FIG. 3, in particular, porous plug 27 is basically a cylindrically shaped disk which snugly fits around interior portion 40 of the second needle cannula while it is seated in recess 51. It is arranged to cover access opening 42 when spring member 26 is in the normal expanded static condition. Moreover, porous plug 27 is preferably designed to allow air, but not blood or other fluids, to pass into access opening 42. Accordingly, this porous plug is made from a material intended to be gas-permeable, liquid-impermeable, and preferably air-permeable and blood impermeable. These permeability properties would allow air to pass therethrough which preventing blood from flowing through this vent structure. Although other materials may be used, it is preferred that plug 27 be made of porous material, such as sintered polyethylene having a general pore rating of about 10 microns.

While the preferred embodiment of this invention includes porous plug 27 as just described, it could be eliminated from this assembly without prejudicing the essential operation of the multiple sample needle assembly. Other ways to eliminate air inside chambe can be devised which fall within the purview of the present invention. For example, a small hole may be included through wall portion 34 surrounding chamber 28. Various techniques such as the inclusion of a hydrophobic membrane over such hole would allow air to pass out of chamber 28 into the surrounding atmosphere. In such a design, plug 27 need not be porous at all; it could merely be an elastomeric material, such as rubber or the like, in order to snugly surround interior portion 40 and effectively cover access opening 42 to prevent blood from flowing into the access opening in the normal, static condition. It can be seen that it may be possible to eliminate plug 27 altogether, and construct protruding portion 36 in snug fashion around interior portion 40 of the second needle. This would assure that access opening 42 is covered in the normal, static condition of the assembly thereby preventing blood from flowing from the chamber into the access opening in this position.

Turning now to FIG. 4, the preferred needle assembly 10 is illustrated connected to a multiple sample holder 19. Cannula 14, extending from forward end 24, is shown inserted into a patient P during the venipuncture procedure. At this time, the needle assembly is in the normal, static condition so that spring member 26 is biasing the second needle cannula outwardly, as illustrated in FIG. 3. Under normal tourniquet pressure, blood from the patient is forced through cannula 14 into forward end 24 of the housing and then into chamber 28. Any air which may be initially inside chamber 28 will then be forced out by the entering blood through porous plug 27, which is air-permeable, but blood-impermeable. Blood fills chamber 28 by flowing through the spaces between leaf springs 49. With at least forward end 24, or a portion thereof, such as wall portion 34, being translucent, the user of this needle assembly can then view the blood as it enters chamber 28. As soon as the user sees the blood in the chamber, it serves as an indication that vein entry has been made. Conversely, if the user does not use blood flow into the chamber, after needle cannula 14 has been inserted into the patient, it can safely be assumed that unsatisfactory vein entry has been accomplished. With this feature, the user does not have to attach an evacuated blood collection container until vein entry indication has been determined. No blood will flow through second needle cannula 15 inasmuch as access opening 42 is sufficiently covered when the second needle cannula is biased in the outward position. Once the user is satisfied that vein entry has been made, evacuated blood collection container 16 is slid into holder 19 so that exterior portion 39 of the second needle cannula penetrates penetrable stopper 21. This combination is illustrated in FIG. 5.

As soon as the point of exterior portion 39 of the second cannula comes in contact with the leading edge of penetrable stopper 21, continued inward movement of the blood collection container will cause the second needle cannula to slide inwardly. Even after the second cannula penetrates the penetrable stopper of the blood collection container, the friction force between these two components should be sufficient to maintain the second needle cannula in an inward position. However, to assure that such inward position is maintained, the leading edge of penetrable stopper 21 abuts against annular ring 41 causing the ring to come in contact with rearward end 25 of the housing. This assures that the second needle cannula will be displaced inwardly when the evacuated blood collection container is in position inside holder 19. It can be seen that inward displacement of the second needle cannula also causes an inward displacement of access opening 42. As a result, the access opening is no longer covered by plug 27. Therefore, blood inside chamber 28 is free to flow through access opening 42, through second needle cannula 15 and into blood collection container 16. The evacuated condition of the blood collection container facilitates the movement of blood from chamber 28 into the collection container. Inward movement of the second needle cannula also causes a deflection or contraction of leaf springs 49, as illustrated in FIG. 5. These leaf springs cannot be overly deflected since stops 50 abut against the interior wall surrounding the chamber. These stops prevent hub 48 from blocking channel 30 during the blood collecting procedure.

Once blood has been collected in blood collection container 16, this filled container is removed from holder 19 while needle cannular 14 remains inserted in the vein of the patient. Removal of the blood collection container also removes the inward force which caused the second needle cannula to slide inwardly. As a consequence, leaf springs 49 tend to expand or straighten themselves thereby causing hub 48 to push against the second needle cannula and once again urge it outwardly. Access opening 42 is returned to its first position where it is covered by plug 27. These movements automatically cause a prevention of blood from flowing through the second needle cannula. No blood will leak out of this assembly especially during the time period between changes of evacuated blood collection containers. Therefore, the blood will flow from the patient's vein and into chamber 28 until the next blood collection container is inserted into the holder to repeat the inward movement of the second needle cannula as previously described. Once multiple samples of blood have been taken, needle cannula 14 is removed from the patient, whereupon the entire needle assembly is discarded.

Thus, the multiple sample needle assembly of the present invention controls the flow of blood or other liquids therethrough. Blood is prevented from leaking out of this assembly particularly during change of blood collection containers during the multiple sampling procedure. Furthermore, the present invention preferably provides a visual indicator to the user so that a quick determination can be made when the vein has been entered for collection of blood therefrom. These aforementioned features contribute to the efficient use of this type of assembly in the multiple sample collection procedure.

What is claimed is:

1. A multiple sample needle assembly for determining vein entry when collecting blood samples from a patient comprising:
    a housing having a forward end, a rearward end and a chamber within, said housing being translucent at least around the chamber so that said chamber is viewable by a user of said assembly;
    a first cannula in fluid communication with said chamber extending outwardly from said forward end and adapted for insertion into a patient;
    a second cannula positioned in said rearward end and slidable from a first position to a second position and having a first end portion extending outwardly from said rearward end and a second end portion opposite said first end portion and extending inwardly into said chamber the end of said second end portion being blocked;
    an access opening in said second end portion providing flow communication between the lumen of said second cannula and said chamber; a plug of material in said rearward end of said chamber and tightly surrounding said second end portion for preventing liquid communication through said access opening when said second cannula is in said first position, but providing fluid communication between said chamber and the lumen of said second cannula through said access opening when said second cannula is in said second position inwardly displaced from said first position;
    resilient means inside said chamber normally biasing said second cannula in an outward direction to said first position, said resilient means adapted to contract when said second cannula slides inwardly under an applied force to said second position, said resilient means adapted to urge said second cannula outwardly, when said applied force is removed, to said first position and
    said plug of material being air pervious and liquid impervious.

2. The assembly of claim 1 wherein the access opening is through the side of said second end portion of said second cannula.

3. The assembly of claim 1 wherein said resilient means includes a hub portion connected to and blocking said second end portion of said second cannula and spring means extending between said hub and the wall of said housing surrounding said chamber, said spring means being normally expanded to bias said second cannula outwardly.

4. The assembly of claim 3 wherein said spring means is a plurality of leaf springs radially extending from said hub.

5. The assembly of claim 1 wherein the entire housing is translucent.

6. The assembly of claim 1 wherein said first end portion of said second cannula includes an annular ring around its periphery to said movement of said second cannula inwardly during use.

7. The assembly of claim 1 wherein the housing includes means for connecting a holder for an evacuated container.

8. The assembly of claim 7 which further includes a holder for an evacuated container connected to said housing.

* * * * *